United States Patent [19]
Holbert et al.

[11] Patent Number: 4,920,114
[45] Date of Patent: Apr. 24, 1990

[54] 19-FLUORO- OR CYANO-21-HYDROXYPROGESTERONE DERIVATIVES USEFUL AS 19-HYDROXYLASE INHIBITORS

[75] Inventors: Gene W. Holbert, Loveland; J. O'Neal Johnston, Milford, both of Ohio

[73] Assignee: Merrell Dow Pharmaceuticals Inc., Cincinnati, Ohio

[21] Appl. No.: 212,410

[22] Filed: Jun. 28, 1988

[51] Int. Cl.$^5$ .................. C07J 1/00; A61K 31/56
[52] U.S. Cl. .................. 514/177; 514/178; 514/179; 514/182; 514/181; 552/539; 552/526; 552/515; 552/561; 552/588; 552/587; 552/583; 552/600; 552/601; 552/602
[58] Field of Search ............ 260/397.47, 397.3, 397.4, 260/397.45, 397.5; 514/177, 178, 179, 181, 182

[56] References Cited

U.S. PATENT DOCUMENTS

| | | | |
|---|---|---|---|
| 3,124,574 | 3/1964 | Bowers | 260/239 |
| 3,154,569 | 10/1964 | Ercoli et al. | 260/397.3 |
| 3,159,620 | 12/1964 | Ercoli et al. | 260/397.3 |
| 3,186,988 | 6/1965 | Bowers | 260/239 |
| 3,214,427 | 10/1965 | Ercoli et al. | 260/397.3 |
| 3,257,389 | 6/1966 | Bowers | 260/239 |
| 3,257,435 | 6/1966 | Bowers et al. | 260/397.47 |
| 3,394,128 | 7/1968 | Edwards | 260/397.3 |

*Primary Examiner*—Joseph A. Lipovsky
*Attorney, Agent, or Firm*—John J. Kolano

[57] ABSTRACT

19-Fluoro- and cyano- substituted 21-hydroxyprogesterone derivatives and related compounds which are active as 19-hydroxylase inhibitors and useful as antihypertensive agents are described herein. The compounds are prepared using appropriate synthetic pathways which will vary according to the nature of the specific 19-substituted progesterone or related compound desired.

4 Claims, No Drawings

19-FLUORO- OR CYANO-21-HYDROXYPROGESTERONE DERIVATIVES USEFUL AS 19-HYDROXYLASE INHIBITORS

BACKGROUND OF THE INVENTION

19-Nordeoxycorticosterone (19-norDOC) has been found to show much higher hypertensive activity compared to deoxycorticosterone (DOC) [Funder et al., *Endocrinology*, 103, 1514 (1978)]. It is equipotent to aldosterone in stimulating Na+ transport across toad bladder epithelia [Perrone et al., *Am. J. Physiol.*, 41, E406 (1981)] and has two to five times the potency of DOC in Na-retaining activity [Kagawa et al., *Soc. Exp. Biol. Med.*, 94, 444 (1957)].

19-norDOC has been isolated from rats with adrenal regenerating hypertension (ARH) [Gomez-Sanchez et al., *Endocrinology*, 105, 708 (1979)] and from humans [Dale et al., *Steroids*, 37, 103 (1981)]. Elevated excretion of the compound has been reported for three hypertensive rat models: ARH, spontaneously hypertensive rats (SHR) and the salt-susceptible inbred Dahl rat [Griffing et al., *Endocrinology*, 121, 645 (1987); Dale et al., *Endocrinology*, 110, 1989 (1982); Gomez-Sanchez et al., *J. Steroid Biochem.*, 25, 106 (1986)]. Increased levels of urinary 19-norDOC have been observed for several classes of human hypertensives [Griffing et al., *J. Clin. Endocrinol. Metab.*, 56, 218 (1983)].

In the biosynthetic formation of 19-norsteroids, such as 19-norDOC, the initial step is the adrenal 19-hydroxylation of an appropriate steroid such as DOC. Thus, the inhibition of the biosynthetic formation of 19-norDOC by inhibition of 19-hydroxylation of DOC would thus serve to decrease the level of 19-norDOC present in the animal involved and reduce hypertensive effects attributable to the presence of this material.

It has further been shown that 10-(2-propynyl)estr-4-ene-3,17-dione (a known aromatase inhibitor and a 19-hydroxylase inhibitor) retards the development of hypertension and reduces the levels of urinary free 19-norDOC when administered to weanling SHR rats [Melby et al., *Hypertension*, 10, 484 (1987)].

SUMMARY OF THE INVENTION

The present invention relates to 19-nordeoxycorticosterone inhibitors which are 21-hydroxy progesterone derivatives having fluoro substitution or a cyano group at the 19-position or with the 19-methyl replaced by a cyano group. The 21-hydroxy group is optionally esterified and the compounds are optionally oxygenated at the 11-position.

DETAILED DESCRIPTION OF THE INVENTION

The present invention relates to compounds of the formula

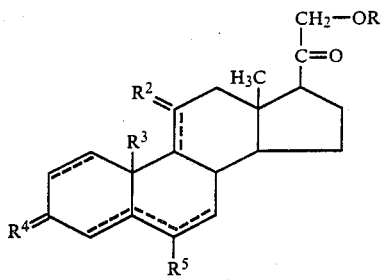

wherein R is hydrogen or

$R^2$ is (H)(H), (H)(OH) or O; $R^3$ is difluoromethyl, cyanomethyl or cyano; $R^4$ is =O, (H)(OH), (H)(OR$^8$), or =CH$_2$; $R^5$ is hydrogen, amino, hydroxy, oxo or methylene; $R^6$ is C$_{1-6}$ alkyl, C$_{5-7}$ cycloalkyl or phenyl; $R^8$ is C$_{2-10}$ alkanoyl; and each of the dotted lines indicate the optional presence of a double bond with the proviso that a 5,6-(double bond) is present only when $R_4$ is (H)(OH) or when there is no double bond at the 4,5-position or 6,7-position and with the proviso that a 9,11-double bond can be present only when $R^2$ is (H)(H).

The C$_{1-6}$ alkyl groups referred to above can be straight or branched-chain and can be exemplified by methyl, ethyl, propyl, isopropyl and butyl. The C$_{5-7}$ cycloalkyl groups can be illustrated by cyclopentyl, cyclohexyl or cycloheptyl. Illustrations of the C$_{2-10}$ alkanoyl groups are acetyl, propionyl, butanoyl, hexanoyl, octanoyl and decanoyl.

The compounds of the present invention can be prepared from the appropriate steroid 17-ketone. Thus, for example, 3,3-ethylenedioxy-19,19-difluoroandrost-5-en-17-one is reacted with methyl methoxyacetate and lithium diisopropylamide whereupon the indicated acetate ester (i.e., the methylene group thereof), adds across the 17-ketone to give the 17-substituted 17-hydroxy steroid. Dehydration introduces a 17-exocyclic double bond and the resulting α-methoxy ester is reduced with DIBAL to the corresponding 2-methoxy ethanol which is then further treated with acid to hydrolyze the enol ether and give the desired 21-hydroxy-20-oxopregnane. In a variation on this procedure, it is possible to use the 3-ethoxy-3,5-diene corresponding to the above 3,3-ethylenedioxy compound. The 17-ketone is then reacted as above to ultimately give, after removal of the various protecting groups, the same product as described above.

The 3,3-ethylenedioxy compound used as the starting material above can be obtained from 19,19-difluorotestosterone benzoate by the following procedure. The 3-ketone is protected as the ethylene ketal by standard procedures and then the 17-benzoate is hydrolyzed using lithium hydroxide. Swern oxidation of the resulting 19-hydroxy compound then gives the desired 19-ketone.

The 3,3-ethylenedioxy-19-cyanoandrost-5-en-17-one used as the starting material for the preparation of the 19-cyano compounds is obtained by the following procedure. 19-Hydroxyandrost-4-ene-3,17-dione is treated with triflic anhydride (trifluoromethanesulfonic anhydride) to form the corresponding 19-triflate ester which then forms the nitrile (19-cyano compound) upon heating in the presence of a cyanide such as sodium cyanide. The nitrile is then ketalized using ethylene glycol to give the 3,17-bis ethylene ketal and this bis-ketal is selectively hydrolyzed using 0.3% perchloric acid in t-butanol to remove the 17-ketal and give the desired 19-cyano-3,3-ethylenedioxyandrost-5-en-17-one.

Similar 10-cyano compounds can be obtained by starting with 19-hydroxyandrost-4-ene-3,17-dione. The two keto groups in this molecule are protected as such or reduced to the corresponding alcohol and appropriately protected while the following series of reactions is carried out. Thus, the 19-hydroxy is oxidized to the aldehyde which is then converted to the corresponding oxime. Dehydration of the oxime then gives the desired cyano compound.

Various other compounds of the present invention can be obtained by specific procedures as follows:

Esters of 21-hydroxy compounds are obtained by standard methods, i.e., by treatment of the alcohol with the appropriate acid chloride or anhydride in the presence of a tertiary amine such as pyridine or triethylamine. Additional solvent (for example, dichloromethane) is optional as is the addition of a catalytic amount of 4-dimethylaminopyridine.

The 11$\beta$-hydroxy compounds of the present invention are prepared by incubation of an appropriate steroid starting material with an appropriate microorganism that will introduce the indicated substitution. The starting steroid selected can be one that will give the desired product directly or the steroid may contain various substituents or protecting groups which are removed after the introduction of the 11-hydroxy group to give the product desired. 11$\alpha$-Hydroxy compounds are obtained in the same manner. 11-Keto compounds are readily obtained by oxidation of the 11$\alpha$- or 11$\beta$-alcohols described above. $\Delta^{9(11)}$-Compounds are obtained by acid catalyzed dehydration of 11$\beta$-alcohols, or their precursors, by standard methods. By precursors of 11$\beta$-alcohols is meant compounds containing an 11-hydroxy group with other substitution or protecting groups present in the molecule, with those other groups being removed after the process described above has been carried out.

To obtain the 3$\beta$-hydroxy-$\Delta^5$-compounds, the following procedure is used. 3,3-Ethylenedioxy-19,19-difluoroandrost-5-en-17-one is reduced with sodium borohydride and the resulting 17-alcohol is converted to the 17-acetate by standard procedures. Brief exposure of this compound to aqueous acetic acid at 60° C. removes the ketal protecting group to give the 3-keto-$\Delta^5$-compound containing some of the corresponding 3-keto-$\Delta^4$-isomer. This ketone is reduced with a hydride such as sodium borohydride to give the corresponding 3-hydroxy compound which is silylated with t-butyldimethylsilyl chloride to give the corresponding 3-(t-butyldimethylsiloxy) compound. The 17-ester is then hydrolyzed to the corresponding alcohol and the alcohol is oxidized to the corresponding 17-ketone, both by standard procedures. The hydroxyacetyl side chain is introduced at the 17-position using methyl methoxyacetate and the general procedure described earlier.

To obtain the 3$\beta$-hydroxy-$\Delta^4$-compounds, 3,3-ethylenedioxy-19,19-difluoroandrost-5-en-17-one is reduced with sodium borohydride and the resulting 17-alcohol is treated with acid to remove the 3-ketal. The resulting compound is silylated with t-butyldimethylsilyl chloride to give the corresponding 17-(t-butyldimethylsilyloxy) compound which is reduced with diisobutylaluminum hydride to give the corresponding 3$\beta$-hydroxy compound. This alcohol is converted to the correspond 3-acetate and the 17-silyloxy group is removed, both by standard procedures, to give the 17-alcohol. This is then oxidized to the 17-ketone by standard procedures and a 17-hydroxyacetyl side chain is introduced using methyl methoxyacetate and the general procedure described earlier. The 3-esters can be obtained by esterification of the appropriate 3-hydroxy compound.

To obtain the compounds of the present invention in which R$^4$ is =CH$_2$, 19,19-difluoro-17$\beta$-hydroxyestr-4-en-3-one is used as the starting material. This testosterone derivative is subjected to a Wittig reaction to give 19,19-difluoro-3-methyleneestr-4-en-17$\beta$-ol. The 17-hydroxy group is then oxidized to the corresponding ketone and a hydroxyacetyl side chain is introduced at the 17-position using methyl methoxyacetate and the general procedure described earlier.

Compounds containing multiple double bonds in the steroid ring system can be obtained by the dehydrogenation of the appropriate starting compound. Thus, for example, 19,19-difluoro-21-hydroxypregn-4-ene-3,20-dione can be dehydrogenated with 2,3-dichloro-5,6-dicyanobenzoquinone in dioxane to give the corresponding 1,4-diene. Dehydrogenation of the same compound with chloranil in t-butanol gives the corresponding 4,6-diene. Subsequent exposure of the 4,6-diene to 2,3-dichloro-5,6-dicyanobenzoquinone in dioxane leads to the corresponding 1,4,6-triene.

The 6-amino compounds of the present invention are prepared from 19,19-difluoro-21-hydroxypregn-4-ene-3,20-dione by the following procedure. The indicated 4-enedione is acetylated to give the corresponding 21-acetate ester. This ester is reacted with ethyl orthoformate and p-toluenesulfonic acid to give the corresponding 3-ethoxy-3,5-diene. When an ethanolic solution of this 3,5-diene is exposed to sunlight in the presence of air, the corresponding 6$\beta$-hydroxy-3-keto-$\Delta^4$-compound is formed. This compound is converted to the corresponding 3,20-bis-ethylene ketal which is then oxidized to the 6-ketone. Reaction of this 6-ketone with hydroxylamine hydrochloride gives the oxime which is then reduced using zinc and acetic acid to produce the corresponding 6$\beta$-amino compound. The various ester and ketal protecting groups are then removed by standard procedures to give the desired 6$\beta$-amino product. The protecting groups can also be removed from the 6-ketone intermediate to give the 3,6,20-triketone product. The protected 6-ketone intermediate can also be subjected to a Wittig reaction to give the corresponding 6-methylene compound.

The compounds of the present invention are useful as 19-hydroxylase inhibitors and antihypertensive agents. Specifically, the inhibitory activity of the present compounds toward adrenal 19-hydroxylase is demonstrated by an in vitro radioenzymatic assay. The test compounds are solubilized in buffer/solvent media at concentrations ranging from 1 nM to 50 $\mu$M, then added to assay tubes containing an adrenal mitochondrial suspension, i.e., rat, hamster, bovine, primate, or human, etc., an NADPH-generating system, and radiolabeled deoxycorticosterone. The assay components are incubated for varying time intervals at 25°–37° C. and the reaction is quenched. The hydroxylated corticoids [i.e., 19-HO-DOC (19-hydroxydeoxycorticosterone), 18-HO- DOC(18-hydroxydeoxycorticosterone) and corticosterone] are extracted with organic solvent and isolated by standard chromatographic procedures. The inhibition of 19-hydroxylation is estimated from comparison of buffer control assay tubes with assay tubes containing the inhibitor compounds. The inhibitor concentrations producing 50% inhibition ($IC_{50}$) are determined.

In addition, the activity of the present compounds as antihypertensive agents is demonstrated by the following test procedure. Male spontaneously hypertensive rats (SHR) at the age of 4½ weeks were used. The rats were housed in metabolic cages, one rat per cage, and maintained on a diet of regular Purina Rat Chow and tap water in a constant-temperature environment with 12-hour light/dark cycles. One group of six rats received daily subcutaneous injections of test compound, 10 mg/kg body weight, prepared in 5% ethanol and olive oil and sonicated. Seven control SHR were given injections of vehicle. The rats receive treatment for several weeks with daily injections of test compound in the test SHR and of vehicle in control SHR.

Systolic blood pressures (SBPs) of the conscious, unstressed animals were recorded using a physiograph coupled to a tail cuff and photocell transducer in a sound-resistant constant-temperature environment, starting at 3 weeks of treatment. Rats were habituated to the procedure during several training sessions. The first reliable SBP measurements were made at the age of 7–8 weeks.

To achieve a desired effect, such as an antihypertensive effect, the compounds of the present invention can be administered orally, parenterally, for example, intramuscularly and subcutaneously, to a patient in need of treatment. The term patient is taken to mean a warm-blooded animal, for example, mammals such as rats, mice, dogs, cats, horses, pigs, cows, sheep, primates and humans. The compounds of the invention can be administered alone or suitably admixed in the form of a pharmaceutical preparation to the patient being treated. The amount of compound administered will vary with the severity of the condition and repetitive treatment may be desired. For oral and parenteral administration the amount of compound administered, that is, the effective antihypertensive amount, is from 0.1 to 150 mg/kg of body weight per day and preferably from 1 to 50 mg/kg of body weight per day. Unit dosages for oral or parenteral administration may contain, for example, from 5 to 250 mg of the active ingredient. The compounds can be administered alone or in combination with one another.

For oral administration the compounds can be formulated into solid or liquid preparations, such as, capsules, pills, tablets, troches, powders, solutions, suspensions or emulsions. The solid unit dosage forms can be a capsule which can be of the ordinary gelatin type containing the active compound and a carrier, for example, lubricants and inert filler such as lactose, sucrose and corn starch. In another embodiment, an active compound of the invention can be tableted with conventional tablet bases such as lactose, sucrose and corn starch in combination with binders such as acacia, corn starch or gelatin, disintegrating agents such as potato starch or alginic acids and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanols and glycols, such as, propylene glycol or polyethylene glycol are preferred liquid carriers, particularly for injectable solutions.

The compounds can be administered in the form of a depot injection or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones, for example, Silastic, silicone rubber manufactured by the Dow-Corning Corporation. Further information on suitable pharmaceutical carriers and formulation techniques are found in standard texts, such as *Remington's Pharmaceutical Sciences*, Mack Publishing Company, Easton, Pa.

The following examples are provided to illustrate the present invention. They should not be construed as limiting it in any way.

EXAMPLE 1

19,19-Difluorotestosterone benzoate (4.29 g) is dissolved in 100 ml of benzene and there is added 2.8 ml of ethylene glycol and 0.21 g of p-toluenesulfonic acid. The rapidly stirred mixture is heated at reflux for six hours under a Dean-Stark water separator under an argon atmosphere. Upon cooling, 1 ml of pyridine is added and the solution is poured into saturated sodium carbonate solution. Ether is added and the layers are separated. The organic phase is washed three times with water and once with brine, dried over magnesium sulfate, and concentrated. The residue is crystallized from ethanol to afford 3,3-ethylenedioxy-19,19-difluoroandrost-5-ene-17β-ol benzoate as white crystals.

A solution of this 3,3-ethylenedioxy ester (4.73 g) in 50 ml of tetrahydrofuran is chilled to 0° C., treated with 10 ml of 1N lithium hydroxide in methanol and allowed to warm to room temperature. The reaction is monitored by thin layer chromatography. When all of the ester has been hydrolyzed, the solution is concentrated and diluted with ether. The mixture is washed three times with water and once with brine, dried over magnesium sulfate, and concentrated. The residue is crystallized from ethyl acetate/hexane to yield 3,3-ethylenedioxy-19,19-difluoroandrost-5-en-17β-ol as white crystals.

A solution of the 17β-ol (3.68 g), prepared as above, in dichloromethane is subjected to Swern oxidation using dimethyl sulfoxide and oxalyl chloride according to the procedure described by Mancuso et al., *J. Org. Chem.*, 43, 2480 (1978). The crude product obtained is crystallized from ethanol to give 3,3-ethylenedioxy-19,19-difluoroandrost-5-en-17-one.

Methyl methoxyacetate (8.33 g) is dissolved in 25 ml of tetrahydrofuran and added dropwise over 5–10 minutes to a solution of lithium diisopropyl amide which has been prepared from 14.1 ml of diisopropylamine and a commercially available solution of n-butyllithium in hexane (2.5M, 40 ml) in 100 ml of tetrahydrofuran at −78° C. A solution of 3.66 g of the 17-ene obtained in the preceding paragraph in 33 ml of tetrahydrofuran is then added dropwise over 10–15 minutes, and the solution is stirred at −78° C. for 3 hours. The reaction is quenched by pouring it into saturated aqueous ammonium chloride and then extracted into dichloromethane. The extract is washed with brine, dried over magnesium sulfate, and concentrated. The resulting oil is subjected to column chromatography on silica gel using hexane:ethyl acetate (7:3) as eluent to yield the addition product as a mixture of epimers.

Without further purification, the addition product is dissolved in 35 ml of pyridine, chilled to −20° C. and treated with 3.3 ml of thionyl chloride. The solution is stirred for 45 minutes at −20° C., poured into ice water, and extracted with dichloromethane. The extract is washed with brine, dried over magnesium sulfate, and concentrated. Silica gel chromatography using hexane:ethyl acetate (8:2) as eluent affords methyl 3,3-ethylenedioxy-19,19-difluoro-20-methoxypregna-5,17(20)-dien-21-oate as a mixture of isomers.

A solution of the 21-oate (4.53 g) in 50 ml of toluene is chilled to −20° C. and treated with 20 ml of a commercially available solution of diisobutylaluminum hydride in hexane (1M). After stirring at −20° C. for 1 hour, the solution is treated dropwise with a saturated aqueous solution of sodium potassium tartrate until a white granular solid is formed. Solid sodium sulfate is added to absorb excess water and the mixture is stirred at room temperature for 1 hour. The solids are filtered off and washed thoroughly with toluene. The combined filtrates are concentrated and the residue is purified by silica gel chromatography, eluting with ethyl acetate/hexane, to afford 3,3-ethylenedioxy-19,19-difluoro-20-methoxy-21-hydroxypregna-5,17(20)-diene as a white solid.

The 21-hydroxy compound (4.25) g obtained as above, is dissolved in 475 ml of methanol, treated with 1N hydrochloric acid and stirred overnight. The bulk of the methanol is removed under reduced presure and the remaining suspension is partitioned between dichloromethane and water. The organic phase is washed twice with water and then with brine and dried over magnesium sulfate. The residue obtained upon concentration is crystallized from ethyl acetate/hexane to afford 19,19-difluoro-21-hydroxypregn-4-ene-3,20-dione (19,19-difluoro-11-deoxycorticosterone) as white crystals. This compound has the following structural formula:

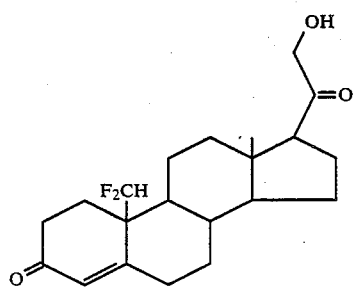

What is claimed is:
1. A compound of the formula

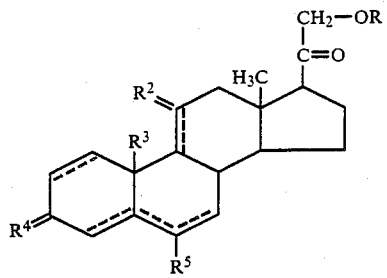

wherein R is hydrogen or

$R^2$ is (H)(H), (H)(OH) or O; $R^3$ is difluoromethyl, cyanomethyl, or cyano; $R^4$ is =O, (H)(OH), (H)(OR$^8$), or =CH$_2$; $R^5$ is hydrogen, amino, hydroxy, oxo or methylene; $R^6$ is C$_{1-6}$ alkyl, C$_{5-7}$ cycloalkyl or phenyl; $R^8$ is C$_{2-10}$ alkanoyl; and each of the dotted lines indicate the optional presence of a double bond with the proviso that a 5,6-(double bond) is present only when R$_4$ is (H)(OH) or when there is no double bond at the 4,5-position or 6,7-position and with the proviso that a 9,11-double bond can be present only when $R^2$ is (H)(H).

2. A compound according to claim 1 which has the formula

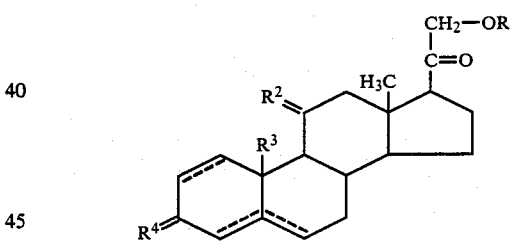

wherein R is hydrogen or

$R^2$ is (H)(H), (H)(OH) or O; $R^3$ is difluoromethyl; $R^4$ is =O, (H)(OH) or =CH$_2$; $R^6$ is C$_{1-6}$ alkyl, C$_{5-7}$ cycloalkyl or phenyl; and each of the dotted lines indicate the optional presence of a double bond with the proviso that a 5,6-(double bond) is present only when R$_4$ is (H)(OH) or when there is no double bond at the 4,5-position.

3. A compound according to claim 1 which is 19,19-difluoro-21-hydroxypregn-4-ene-3,20-dione.

4. A method for treating hypertension in animals which comprises administering to an animal in need of such treatment an antihypertensive amount of a compound of the formula

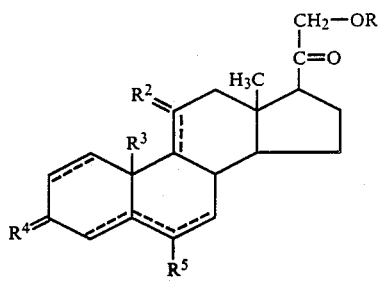

wherein R is hydrogen or

$R^2$ is (H)(H), (H)(OH) or O; $R^3$ is difluoromethyl, cyanomethyl or cyano; $R^4$ is =O, (H)(OH), (H)(OR$^8$), or =CH$_2$; $R^5$ is hydrogen, amino, hydroxy, oxo or methylene; $R^6$ is C$_{1-6}$ alkyl, C$_{5-7}$ cycloalkyl or phenyl; $R^8$ is C$_{2-10}$ alkanoyl; and each of the dotted lines indicate the optional presence of a double bond with the proviso that a 5,6-(double bond) is present only when $R^4$ is (H)(OH) or when there is no double bond at the 4,5-position or 6,7-position and with the proviso that a 9,11-double bond can be present only when $R^2$ is (H)(H).

* * * * *